United States Patent [19]
Hart et al.

[11] Patent Number: 5,584,850
[45] Date of Patent: Dec. 17, 1996

[54] TROCAR HAVING AN ANTI-INVERSION SEAL

[75] Inventors: Charles C. Hart, Huntington Beach; Vincent C. Tangherlini, Rancho Santa Margarita, both of Calif.

[73] Assignee: Applied Medical Resources Corporation, Laguna Hills, Calif.

[21] Appl. No.: 451,022

[22] Filed: May 25, 1995

[51] Int. Cl.$^6$ .................................................. A61B 17/34
[52] U.S. Cl. ............................. 606/185; 604/30; 604/278
[58] Field of Search ...................................... 606/185, 186; 604/196, 246, 30, 31, 34, 167, 256, 169

[56] References Cited

U.S. PATENT DOCUMENTS

| | | |
|---|---|---|
| 4,414,973 | 11/1983 | Matheson et al. . |
| 4,535,819 | 8/1985 | Atkinson et al. . |
| 4,645,494 | 2/1987 | Lee et al. . |
| 4,655,765 | 4/1987 | Swift . |
| 4,762,517 | 8/1988 | McIntyre et al. . |
| 4,765,588 | 8/1988 | Atkinson . |
| 4,773,552 | 9/1988 | Boege et al. . |
| 4,781,680 | 11/1988 | Redmond et al. . |
| 4,827,973 | 5/1989 | Boehmer . |
| 5,295,658 | 3/1994 | Atkinson et al. . |
| 5,342,316 | 8/1994 | Wallace ..................................... 604/167 |
| 5,360,417 | 11/1994 | Gravener et al. ......................... 604/169 |
| 5,407,434 | 4/1995 | Gross ....................................... 604/167 |
| 5,443,452 | 8/1995 | Hart et al. ............................... 604/167 |

*Primary Examiner*—Michael Powell Buiz
*Assistant Examiner*—Kevin Truong
*Attorney, Agent, or Firm*—Richard L. Myers

[57] ABSTRACT

A trocar is adapted to form a seal around a surgical instrument and includes a cannula having an axis extending between a proximal end and a distal end. A seal housing disposed at the proximal end has a proximal wall with a hole extending into the housing. A septum valve disposed within the housing has a normal state when the instrument is absent from the trocar, and a stretched state when the instrument is being withdrawn from the trocar. A spacer extending between the proximal wall and the septum valve, engages the valve at a particular position which separates the valve into an inner portion, which is adapted to form a seal with the instrument and an outer portion, which is adapted to form a seal with the housing. The spacer has an axial length sufficient to space the particular position of the septum wall from the hole in the proximal wall a distance greater than the radial length of the inner portions of the valve in the stretched state. The septum valve can be configured to provide an instrument insertion force less than an instrument withdrawal force.

19 Claims, 3 Drawing Sheets

TROCAR HAVING AN ANTI-INVERSION SEAL

BACKGROUND OF THE INVENTION

1. Field of the Invention

This invention relates generally to trocars and other access devices which provide working channels into body cavities and form seals around instruments introduced into the working channel.

2. Discussion of the Prior Art

Trocars and other access devices are used to provide working channels across body walls and into body cavities, such as the abdominal cavity. A trocar typically includes an elongate tube or cannula which defines the working channel, and which is operatively inserted through the abdominal wall using an obturator. The obturator, with a sharp distal tip, is initially inserted into the working channel of the cannula. This combination is then pressed through the body wall at a puncture site. Finally, the obturator is removed leaving the cannula and its working channel to provide access into the body cavity.

The cavity is typically inflated to a pressure sufficient to enlarge the surgical environment. Maintenance of this inflation pressure is of particular importance to the procedure. With the cannula extending into the inflated cavity, the inflating gas would easily escape were it not for valves which extend across the working channel in a housing of the trocar. Both zero closure valves and septum valves are used for this purpose. These valves are configured to facilitate the introduction of instruments through the trocar while maintaining the inflation pressure by forming appropriate seals with the outer surface of each instrument.

An instrument is first inserted through a hole in a proximal wall of the trocar housing. Within the housing, the septum valve has typically been placed immediately distal of this proximal wall. The septum valve is highly elastomeric and commonly formed from latex which has an ability to stretch as much as 800% These elastomeric characteristics enable the valve to be used with many different instruments having highly variable outside diameters and surface configurations.

Insertion of these instruments through the proximal wall of the housing, the septum valve, zero closure valve, and the working channel has been addressed by many concepts in the prior art. However, it is the removal of the instruments which has been particularly difficult in some cases. When the instrument is removed, the septum valve initially attempts to invert. While this inversion can be tolerated in most instances, it becomes a severe problem if the instrument pulls the septum valve rearwardly where it can bind the instrument in the critical space which is formed between the proximal wall of the housing and the instrument.

This problem is most severe when the critical space is small, for example when the diameter of the instrument is only slightly smaller than the diameter of the hole. The problem is further compounded when the instrument is provided with a surface configuration which increases the coefficient of friction with the septum valve. Grit blasted finishes, which are commonly used to form anti-glare surfaces on instruments, are particularly detrimental to the removal process. Under these conditions, the septum valve has an even greater tendency to be pulled into the critical space. When these conditions exist together, it is often impossible to remove the instrument from the trocar as it is bound by an increasing pressure from the septum. Although the binding effect may be overcome by moving the instrument distally, additional attempts to remove it proximally merely re-create the problem. Under these conditions, it has been necessary to fully remove the entire trocar system in order to withdraw the instrument distally through the working channel. This is particularly aggravating to the surgeon who must then reinsert the trocar to provide the working channel access. Certainly if a surgeon knew that a particular instrument would bind upon removal, he would never insert it. But unfortunately, these circumstances are not easily predictable. Accordingly, the removal problem commonly occurs quite unexpectedly.

SUMMARY OF THE INVENTION

These problems of the prior art are overcome with the present invention which includes a septum valve that is operatively disposed to offer a greater resistance to inversion when the instrument is withdrawn. Even if the septum valve inverts, the valve and housing can be provided with a relationship which maintains the septum valve distally of the proximal hole. As a result even if the septum valve inverts, it cannot reach the critical space between the opening and the instrument, to impede withdrawal of the instrument from the trocar.

Inversion of the septum valve can be inhibited by providing it with a funnel configuration, such as a conical configuration. The valve can be molded in this form and mounted in its operative position in the molded shape. Alternatively, the valve can be formed with a planar configuration but mounted with a radial compression load providing the valve with the preferred funnel shape.

The spacing of the septum valve from the proximal wall of the housing can be addressed with different embodiments of the invention. In one case, the entire septum valve is spaced distally from the proximal wall of the housing. This makes it impossible for the valve to stretch into the critical space between the instrument and the opening. Alternatively, the septum valve can be mounted with its circumferential portions in close proximity to the proximal wall but with an annular flange axially spacing the central portions of the septum valve from the opening. This annular flange, which can be formed on the housing or the septum valve, divides the valve into circumferential portions and central portions which define the opening in the valve. As long as the annular flange has an axial length greater than the stretch potential of the central portions of the valve, the septum valve can not extend into the critical space.

In one aspect of the invention, a trocar is adapted to form a seal around a surgical instrument having an outer surface. The trocar comprises a cannula having an axis extending between a proximal end and a distal end. A housing disposed at the proximal end forms with the cannula a working channel which is sized and configured to receive the instrument. An elastomeric septum valve is disposed in the housing and extends transverse to the axis across the working channel. Portions of the septum valve define a hole having a diameter less than the diameter of the outer surface of the instrument, so that during insertion of the instrument the septum valve forms a seal with the outer surface of the instrument. These portions of the septum valve are configured to exert a first force on the instrument when it is inserted into the working channel of the trocar, and to exert a second force on the instrument when it is withdrawn from the working channel of the trocar. The first insertion force is less than the second withdrawal force.

3

In an additional aspect of the invention, a trocar is adapted to form a seal around a surgical instrument and comprises a cannula having an axis extending between a proximal end and a distal end. A housing having a proximal wall defining a hole, forms with the cannula a working channel sized and configured to receive the instrument. A septum valve, which is disposed in the housing and extends transverse to the axis, has a normal state when the instrument is absent from the working channel and a stretched state when the instrument is withdrawn from the working channel. A spacer extending between the proximal wall of the housing and the septum valve engages the septum valve at a particular position along the valve. This portion of engagement separates the septum valve into an inner portion, which is adapted to form a seal with the instrument, and an outer portion, which is adapted to form a seal with the housing. The spacer has an axial length sufficient to space the particular position of the septum valve from the portions of the proximal wall a distance which is greater that the radial length of the inner portions of the septum valve in the stretched state. In this manner, the spacer prevents the septum valve from reaching the hole in the proximal wall when the instrument is withdrawn.

In a further aspect of the invention, the septum valve has a normal state when the instrument is absent from the working channel and has a stretched state when the instrument is being withdrawn from the working channel. Portions of the proximal wall, which define a hole sized and configured to receive the instrument. An inner edge of the septum valve defines a hole and forms a seal with the surgical instrument. An outer edge of the septum valve, which forms a seal with the housing, is disposed circumferentially of the inner edge and is separated from the inner edge by a first distance when the septum valve is in a stretched state. The outer edge of the septum valve is spaced from the portions of the proximal wall a second distance which is greater than the first distance. This assures that the septum valve is sufficiently spaced from the hole in the proximal wall to prevent binding when the instrument is withdrawn. Outer portions of the septum valve, disposed circumferentially of the inner portions, form a seal with the housing. The outer portions are spaced from the inner portions a first distance when the septum valve is in a stretched state. The outer portions of the septum valve are spaced from the portions of the proximal wall a second distance which is greater than the first distance to prevent the septum valve from reaching the hole in the proximal wall when the instrument is being withdrawn.

These and other features and advantages of the invention will become more apparent with a discussion of preferred embodiments and the best mode of the invention, and reference to the associated drawings.

DESCRIPTION OF PREFERRED EMBODIMENTS AND BEST MODE OF THE INVENTION

Figure 1:
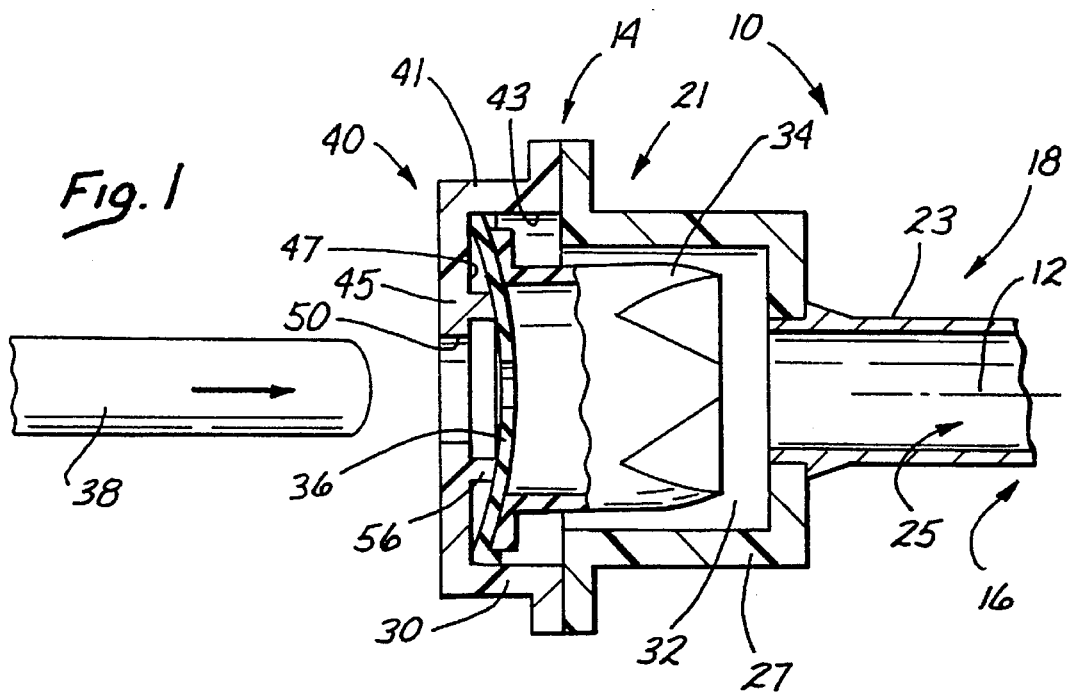
FIG. 1 is an axial cross-section view of a surgical instrument approaching a trocar having a cannula, a valve housing, and a septum valve associated with the present invention.

A trocar is illustrated in FIG. 1 and designated generally by the reference numeral 10. The trocar includes an axis 12 extending between a proximal end 14 and a distal end 16. A cannula 18, disposed at the distal end 16, is coupled to a seal housing 21 disposed at the proximal end 14. In a preferred embodiment, the cannula 18 is formed from stainless steel and has the configuration of a tube 23 which forms a working channel 25 with the housing 21.

The seal housing 21 is commonly formed from rigid plastic and includes a proximal section 27 and a distal section 30 which is glued, snap fit, screwed, or otherwise attached to the proximal section 27. Together the proximal section 27 and distal section 30 define a seal cavity 32 within the housing 21. Within this cavity 32, the trocar 10 typically includes a zero closure valve 34 and a septum valve 36. Both of the valves 34 and 36 function to form seals across the working channel 25; however, they perform this function at different times and in different ways. It is the purpose of the zero closure valve 34 to form its seal across the working channel 25 in the absence of an instrument, such as that designated by the reference numeral 38. In contradistinction, it is the purpose of the septum valve 36 to form its seal across the working channel 25 in the presence of the instrument 38.

The zero closure valve 34 can take any form associated with the prior art. The valve 34 illustrated in FIG. 1 is of the double duck bill variety disclosed and claimed by applicant in PCT application Ser. No. PCT/US93/04709 filed 18 May 1993 and entitled Trocar Valve Assembly.

A subassembly 40 including the septum valve 36 and the proximal section 30 of the housing 27, is of particular interest to the present invention. In the illustrated embodiment, the proximal section 27 has an axial wall 41 with an inner surface 43, and a radial wall 45 with an inner surface 47. The surfaces 43 and 47 define a portion of the cavity 32. In the illustrated embodiment, the radial wall 45 forms a proximal wall of the trocar 10 and defines an opening 50 along the axis 12. This opening 50 also forms part of the working channel 25. A spacer with the configuration of an annular flange 52, which extends distally axially of the proximal wall 45, is discussed in greater detail below.

The septum valve 36 illustrated in FIG. 1 includes portions 61 which define an opening 63 and portions 65 which are disposed circumferentially outwardly of the portions 61.

The opening 63 is similar to the hole 50 in that it is preferably disposed along the axis 12. However, the opening 63 in its natural state will typically be smaller in diameter than the hole 50. Also, the proximal wall 45 is formed from rigid material while the septum 36 is formed from elastomeric material. Accordingly, the opening 63 can stretch in diameter to accommodate instruments, such as the instrument 38, of different size.

Figure 2:
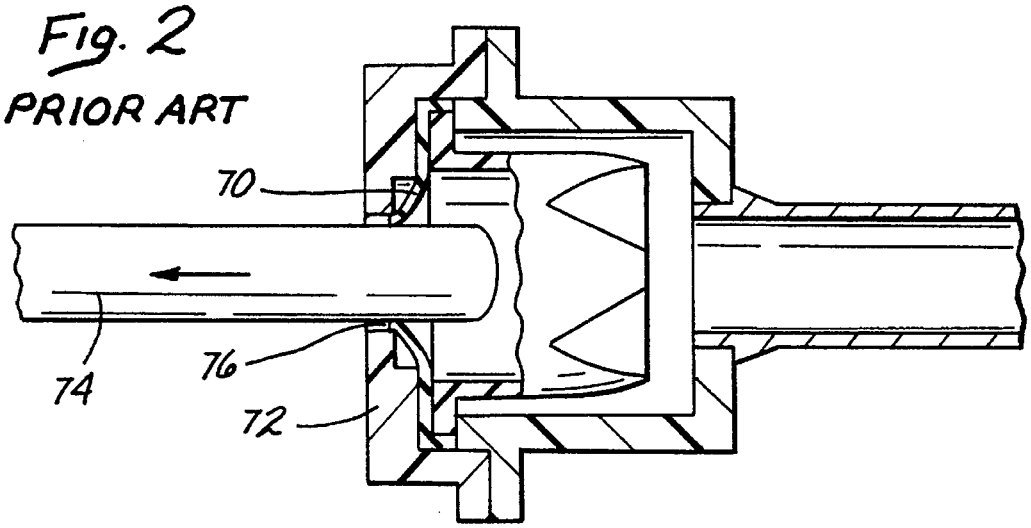
FIG. 2 is an axial cross-section view of a septum valve and housing associated with the prior art.

This construction provides for a spaced relationship between the portions 61 of the septum valve 36 which defines the hole 63, and the portions of the proximal wall 45 which define the hole 50. The importance of maintaining this spaced relationship will be better understood with reference to FIG. 2 which illustrates a construction of the prior art.

In accordance with the prior art, a septum seal 70 having a generally planar configuration is disposed in close proximity to a proximal wall 72 of the housing. An instrument 74 being withdrawn from the working channel would invert the septum seal 70 and draw those portions defining its opening into an annular space 76. This space 76 is defined by the outer surface of the instrument and those portions of the proximal wall 72 which define its opening. This critical space 76, when occupied by the inverted septum 70, tends to bind the instrument 74 against further removal. Unfortunately, the binding effect is enhanced when the outside diameter of the instrument 74 closely approximates the diameter of the hole. This effectively reduced the radial dimension of the critical space 76 thereby increasing the probability of the adverse binding effect. When the instrument 74 is provided with a rough finish, such as a grit blasted finish which is commonly employed to reduce glare, the instrument 74 exhibits an even greater tendency to draw the septum 70 into the critical space 76. Thus the problem of instrument removal is increasingly probable with larger diameter instruments having rough surfaces.

In spite of the fact that the instruments are primarily responsible for the problem in the prior art, the configuration of these instruments must be accepted. Accordingly, the solution of the present invention focuses on the relationship between the proximal wall 45 and the septum valve 36.

Figure 3:
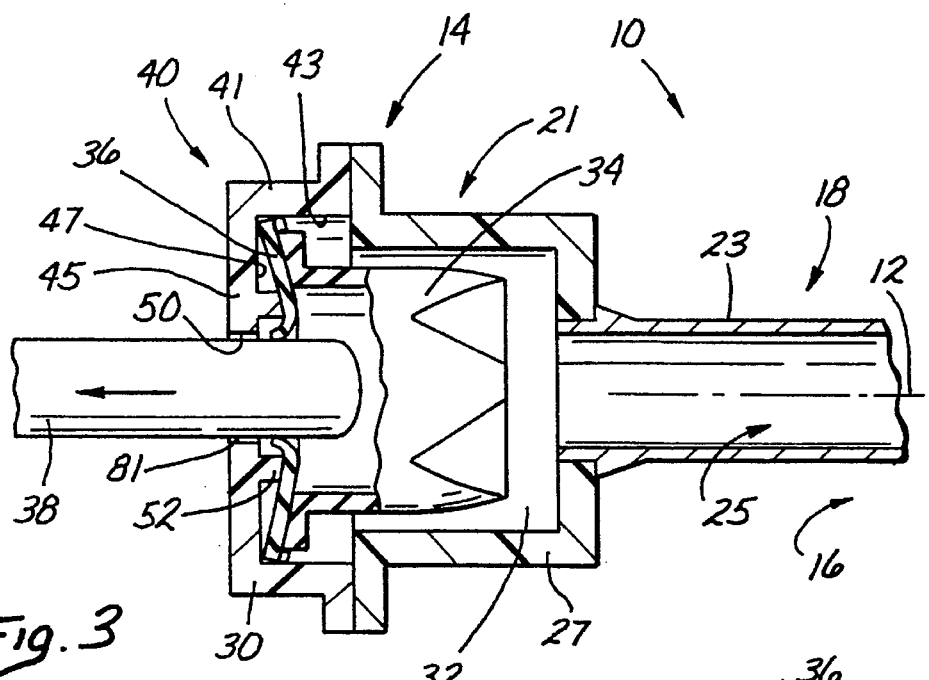
FIG. 3 is an axial cross-section view similar to FIG. 1 and illustrating operation of the valve during removal of an instrument.
Figure 3A:
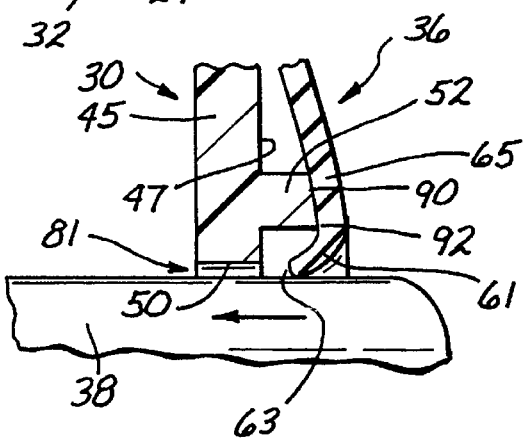
FIG. 3A is an axial cross-section view illustrating an enlarged section of FIG. 3.

Referring now to FIG. 3 and the enlarged view of FIG. 3A, it will be apparent that in accordance with the present invention, the septum valve 36 can be oriented so that the probability of its inversion during instrument withdrawal is greatly reduced. In the unlikely event that inversion does occur, the invention provides for a spaced relationship between the portions of the proximal wall 45 which define the hole 50 and the portion 61 of the septum valve 36 which define the opening 63. Accordingly, even if the septum 36 inverts, it is sufficiently spaced from the hole 50 that it cannot reach the critical space designated generally by the reference numeral 81 in FIG. 3. If the septum valve 36 is incapable of reaching the critical space 81, there will be no binding effect resulting from withdrawal of the instrument 38.

Various embodiments of the invention provide the anti-inversion characteristic of the septum valve 36 and/or the spaced relationship between the valve 36 and the proximal wall 45. In these various embodiments, structural elements similar to those previously discussed will be designated by the same reference numeral followed by a lower case letter. For example, in one aspect of the invention illustrated in FIG. 4, the septum valve is designated by the reference numeral 36a. This valve 36a in the illustrated embodiment has a generally flat planar configuration. The valve 36a includes the central portions 61a which defines the opening 63a as well as the circumferential portions 65a. In this embodiment, the circumferential portions 65a are provided in the form of an annular flange 83 which extends radially outwardly of the portions 61 which define the openings 63.

Figure 5:
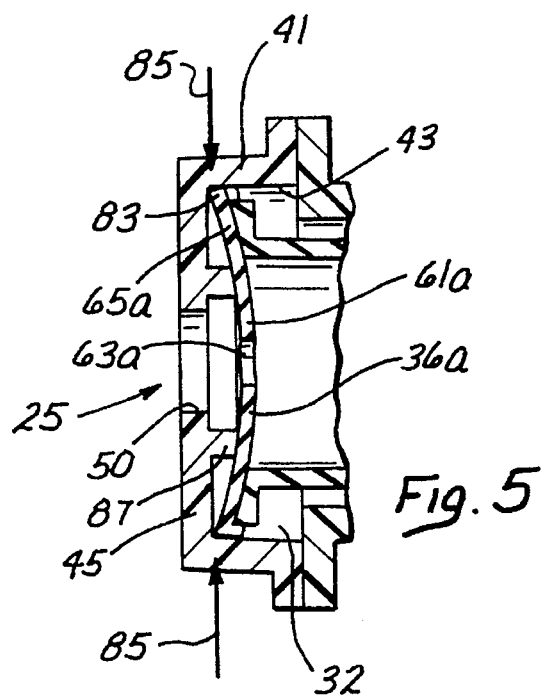
FIG. 5 is an axial cross-section view of the trocar housing with the valve of FIG. 4 operatively disposed in the housing.

The flange 83 is provided with a diameter slightly greater than the diameter of the surface 43 of the axial wall 41 (FIG. 1). As a consequence, when the septum 36a is mounted within the housing cavity 32, the axial wall 41 places a compressive load on the annular flange 83, as illustrated by a pair of arrows 85. This load causes the septum valve 36 to bow inwardly as illustrated in FIG. 5, so that the proximal surface of the valve 36a forms a funnel having, for example, a frustro-conical configuration. In general, this proximal surface of the valve 36a forms an acute angle, less than 90° with respect to the axis 12.

This funnel configuration of the valve 36a can be further enhanced by formation of the annular flange 52 which extends axially inwardly from the proximal wall 45. This flange 52 preferably has an axial length which spaces the central portions 61 of the septum valve 36a a distance from the wall 45 which is greater than the spacing between the radial flange 83 and the wall 45. Thus, both the radial flange 83 and the axial flange 52 facilitate formation of the desired funnel configuration for the valve 36.

With this funnel configuration, the septum valve 36a exhibits different characteristics with instruments which are inserted and removed from the working channel 25. When the instrument 38 (not shown in FIG. 5) is inserted through the opening 63a, there appears to be a lesser resistance to movement than when the instrument 38 is withdrawn. This is believed to result from the funnel configuration of the valve 36a which is structurally oriented to expand for the instrument 38 as it moves in the direction of the funnel, and to slide on the instrument 38 without inverting as the instrument 38 is withdrawn in the opposite direction. Thus the funnelled, bowed, or conical configuration of the septum valve 36 tends to oppose inversion of the valve greatly reducing the probability of the binding effect previously discussed.

Figure 4:
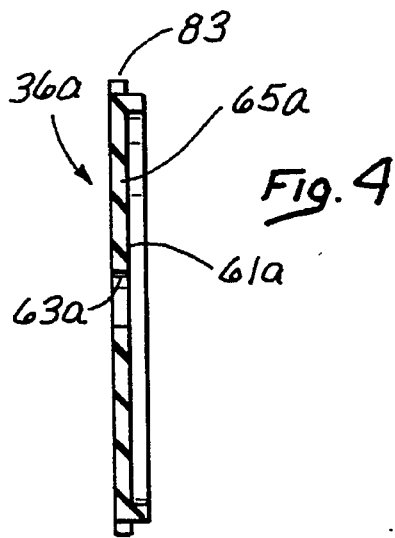
FIG. 4 is an axial cross-section view of a septum valve of the present invention having a generally flat configuration.
Figure 6:
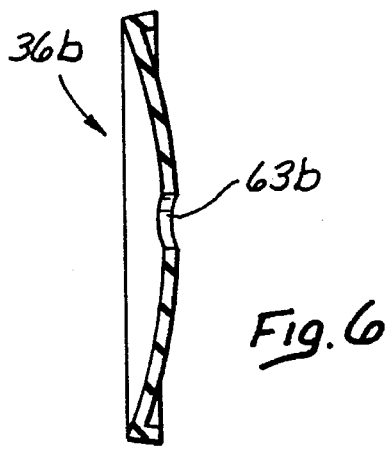
FIG. 6 is an axial cross-section view of a further embodiment of the septum valve of the present invention wherein the valve is molded in a funnel configuration.
Figure 7:
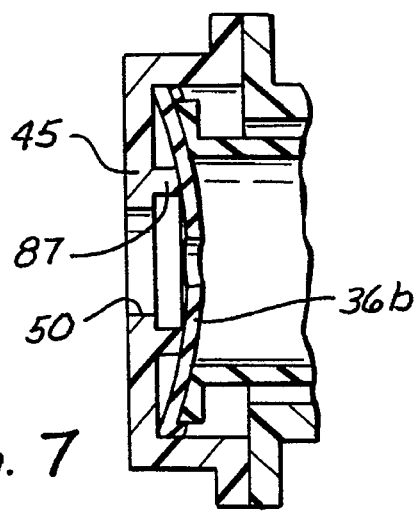
FIG. 7 is an axial cross-section view similar to FIG. 5 but showing the molded valve of FIG. 6 operatively disposed in the housing.

In the embodiment of FIGS. 4 and 5, the septum valve 36 has a planar configuration in its normal state. This normal planar configuration gives way to the desired funnel configuration when the valve 36a is operatively disposed in the housing 21 as illustrated in FIG. 5. In another embodiment illustrated in FIG. 6 and 7, the valve 36b can be molded to provide the desired funnel configuration in its natural state as illustrated in FIG. 6. When the valve 36b is mounted in the operative position, illustrated in FIG. 7, it has the same funnelled, bowed, or conical configuration as it does when it was molded natural state. Thus the embodiment of FIGS. 6 and 7 also has the anti-inversion characteristics resulting from the spaced relationship of the valve portions 61 and the proximal wall 45.

Figure 8:
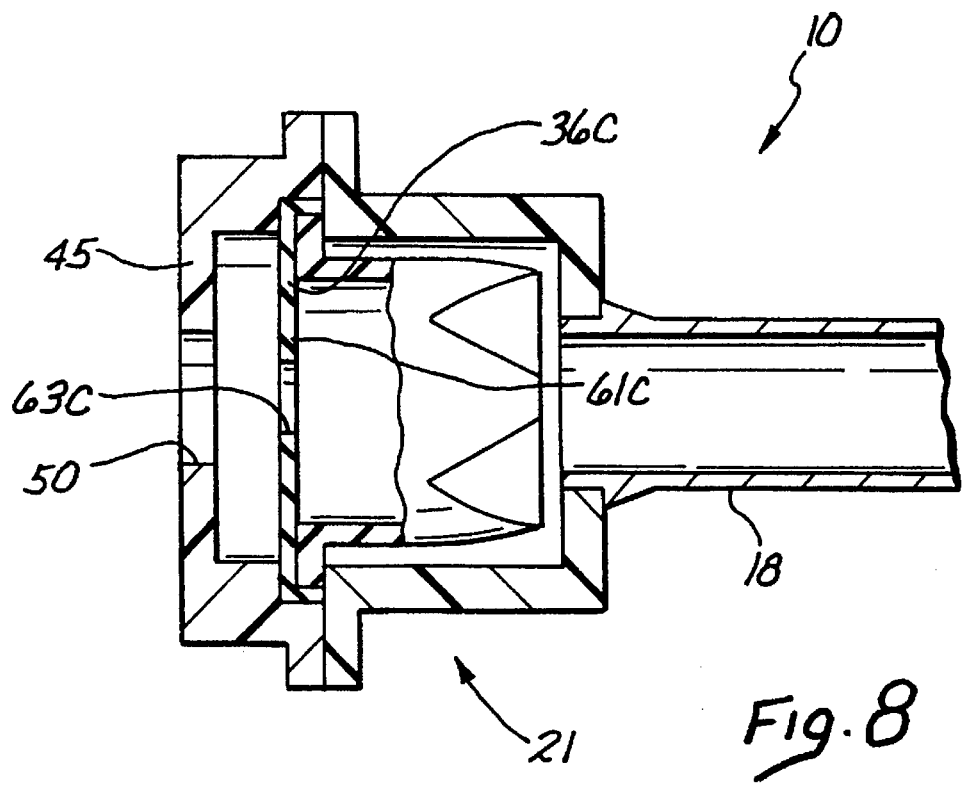
FIG. 8 is an axial cross-section view illustrating a further embodiment of the housing and septum valve combination of the present invention.

With reference to FIG. 8, it will be apparent that even if the septum valve 36 is maintained in a generally parallel relationship with the proximal wall 45, the binding effect can be avoided if the outer edge of the valve 36 is spaced sufficiently from the proximal wall 45. This spacing must be of an axial distance sufficiently long that the inner edge of the central portions 61c, which form the opening 63c cannot reach the hole 50 even when stretched by an instrument having a rough outer surface. This embodiment is quite acceptable where the increased axial length of the seal housing 21 can be tolerated. However, where the size of the trocar 10 and volume of the seal housing 21 is to be minimized, providing the valve 36 with anti-inversion characteristics reduce the requirement for an elongated housing.

The desired spaced relationship is maintained in the preferred embodiment of FIGS. 1 and 3 by the spacer or axial flange 52. In this case, the flange 52 is coaxial with the hole 50 and extends to a distal surface 90, best shown in FIG. 3A. Where the surface 90 of the flange 87 contacts the septum valve 36, the valve is divided between the central portion 61 and the circumferential portion 65. In the illustrated embodiment, the surface 90 is formed with a conical configuration so that it further facilitates the desired funnel configuration of the septum valve 36.

In order for the central portion 61 of the septum valve 36 to reach the critical space 81, the valve 36 must bend around the axial flange 52. To prevent the septum valve 36 from reaching the critical space 81, the axial dimension of the radial flange 52 must be greater than the radial dimension of the central portion 61 in a stretched state. Thus the configuration of the axial flange 52 both in its axial dimension and in its placement along the proximal wall 45 can be critical for a particular embodiment.

In the best mode of the invention where the septum valve 36 in its natural state has a thickness of about 0.04 inches, the axial flange 87 is radially spaced from the hole 50 by about 0.03 inches. The axial length of this flange 87 is about 0.048 inches. Where the inner surface 90 of the axial flange 87 contacts the septum 36, the central portions 61 have a radial diameter of about 0.1 inch. These dimensions seem to be the best compromise between space, probability of valve inversion, and instrument surface configuration, in order to avoid the binding effect.

In general, it is the purpose of the spacer or annular flange 52 to establish a pivot edge which appears as a point 92 in the axial plane of FIG. 3A. This point 92 must be sufficiently spaced from the inner surface 47 of the proximal wall 45 and must contact the septum valve 36 sufficiently close to the opening 63, that the central portion 61 of the valve 36 cannot be stretched to reach the critical space 81 of the hole 50.

Figure 9:
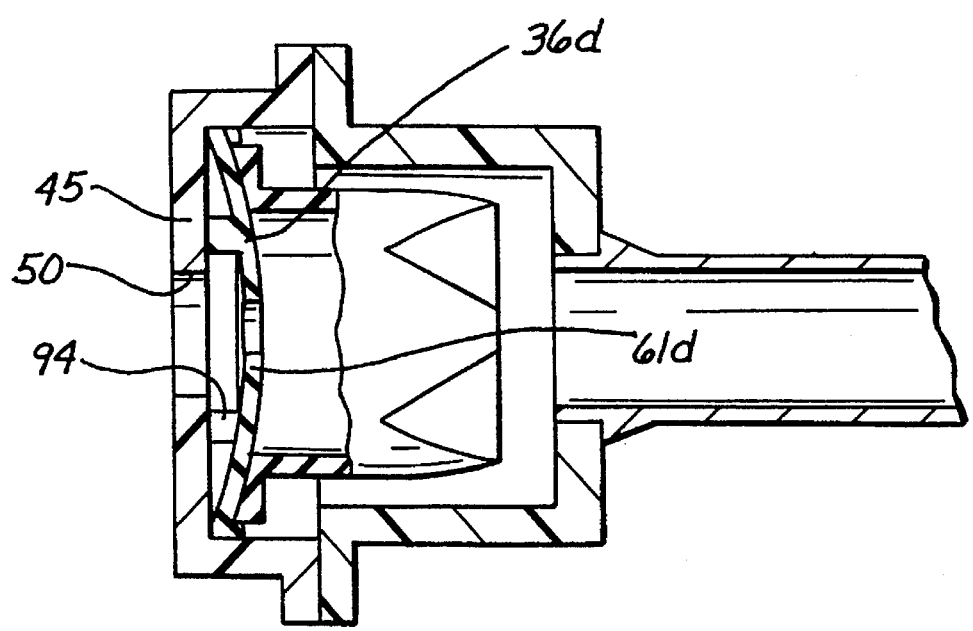
FIG. 9 is an axial cross-section view illustrating an axial spacer formed on the septum valve in a further embodiment of the invention.

The axial flange 52 can take many forms. In the embodiment of FIG. 1, the spacer is formed integral with the proximal wall 45 of the housing 21. In the embodiment of FIG. 9, however, the flange 52 is formed as an integral flange 94 on the septum valve 36d. In both case however, the central portion 61d of the septum valve 36d which extend inwardly of the flange 94 are spaced from the hole 50. The anti-inversion characteristics are the same in either case.

In the foregoing embodiments, the binding effect is inhibited with two structural characteristics. First, providing the septum valve 36 in its operative state with a funnelled, bowed, or conical configuration reduces the tendency of the valve 36 to invert. Without inversion, the central portions 61 remain on the distal side of the valve 36 and consequently do not extend to the critical space 81.

The second structural characteristic contemplates that the valve 36 inverts, and provides for a spaced relationship between at least the central portion 61 of the septum 36 and the wall 45 defining the hole 50.

Of course there are many variations on the foregoing concept which will provide the advantages of the present invention. Whether the septum valve 36 is molded in a flat configuration as illustrated in FIG. 4, or the funnel configuration illustrated in FIG. 6, it is the desired funneled configuration illustrated in both FIGS. 5 and 7 which is to be achieved. Provision of the spacer or flange 52, whether it is integral with the wall 45 or the septum 36, facilitates the funnel configuration for those embodiments which cannot otherwise provide the required spacing as illustrated in FIG. 8. The materials associated with septum valve 46 can also be taken into account. Those materials which have reduced elastomeric properties are less prone to stretching and therefore can achieve the desired benefit with reduced spacing.

Given the wide variations, which are all within the scope of this concept, one is cautioned not to restrict the invention to the embodiments which have been specifically disclosed and illustrated, but rather encouraged to determine the scope of the invention only with reference to the following claims.

We claim:

1. A trocar adapted to form a seal around a surgical instrument having an outer surface, the trocar comprising:

a cannula having an axis extending between a proximal end and a distal end;

a housing disposed at the proximal end of the cannula and forming with the cannula a working channel sized and configured to receive the instrument;

an elastomeric septum valve disposed in the housing and extending transverse to the axis of the cannula across the working channel;

portions of the septum valve defining a hole having a diameter less than the diameter of the outer surface of the instrument so that during insertion of the instrument along the working channel the septum valve forms a seal with the outer surface of the instrument;

the portions of the septum valve being configured to exert a first force on the instrument when the instrument is being inserted into the working channel of the trocar, and to exert a second force on the instrument when the instrument is being withdrawn from the working channel of the trocar; and the first force being less than the second force.

2. The trocar recited in claim 1 wherein the valve has a proximal surface disposed at an acute angle to the axis of the cannula.

3. The trocar recited in claim 1 wherein the portions of the valve define a proximal surface having the configuration of a funnel extending distally to the hole.

4. The trocar recited in claim 3 wherein the funnel is in the shape of a frustrum of a cone.

5. The trocar recited in claim 4 wherein the valve has a molded state and an operative state;

the proximal surface of the valve in the molded state has a generally planar configuration; and the proximal surface of the valve in the operative state has the funnel configuration.

6. The trocar recited in claim 3, wherein:

the valve has a molded state and an operative state;

the proximal surface of the valve in the molded state has the funnel configuration; and the proximal surface of the valve in the operative state has the funnel configuration.

7. The trocar recited in claim 1 further comprising:

a zero closure valve disposed in the housing distally of the septum valve.

8. The trocar recited in claim 7 wherein the zero closure valve is a double duck-bill valve.

9. A trocar adapted to form a seal around a surgical instrument, the trocar comprising:

a cannula having an axis extending between a proximal end and a distal end;

a housing having a proximal wall and forming with the cannula a working channel sized and configured to receive the instrument;

a septum valve disposed in the housing and extending transverse to the axis of the cannula across the working channel, the septum valve having a normal state when the instrument is absent from the working channel and a stretched state when the instrument is being withdrawn from the working channel;

portions of the proximal wall of the housing defining a hole sized and configured to receive the instrument into the working channel;

a spacer extending between the proximal wall and the septum valve, the spacer engaging the septum valve at a particular position separating the septum valve into an inner portion adapted to form a seal with the instrument and an outer portion adapted to form a seal with the housing;

the spacer having an axial length sufficient to space the particular position of the septum valve from the portions of the proximal wall a distance greater than the radial length of the inner portions of the septum valve in the stretched state; whereby the septum valve is prevented from reaching the hole in the proximal wall of the housing when the instrument is withdrawn.

10. The trocar recited in claim 9 wherein the spacer includes an annular flange extending axially of the housing.

11. The trocar recited in claim 10 wherein the spacer is formed integral with the housing.

12. The trocar recited in claim 11 wherein the annular flange has a distal surface with the configuration of a cone.

13. The trocar recited in claim 9 wherein the spacer is formed integral with the valve.

14. The trocar recited in claim 9 further comprising side walls of the housing sized to exert a radial compression force on the valve in the normal state in order to provide the valve with the configuration of a funnel.

15. The trocar recited in claim 9 further comprising:

a zero closure valve disposed in the housing distally of the septum valve.

16. The trocar recited in claim 15 wherein the zero closure valve is a double duck-bill valve.

17. A trocar adapted to form a seal around a surgical instrument, the trocar comprising:

a cannula having an axis extending between a proximal end and a distal end;

a housing having a proximal wall and forming with the cannula a working channel sized and configured to receive the instrument;

a septum valve disposed in the housing and extending transverse to the axis of the cannula across the working channel, the septum valve having a normal state when the instrument is absent from the working channel and having a stretched state when the instrument is being withdrawn from the working channel;

portions of the proximal wall defining a hole sized and configured to receive the instrument into the working channel;

an inner edge of the septum valve defining a hole and adapted to form a seal with the surgical instrument;

an outer edge of the septum valve disposed circumferentially of the inner edge and forming a seal with the housing, the outer edge being spaced from the inner edge a first distance when the septum valve is in the stretched state;

the outer edge of the septum valve being spaced from the portions of the proximal wall a second distance; and the second distance being greater than the first distance to prevent the septum valve from reaching the hole in the proximal wall when the instrument is being withdrawn.

18. A trocar adapted to form a seal around a surgical instrument having an outer surface, the trocar comprising:

a cannula having an axis extending between a proximal end and a distal end;

a housing disposed at the proximal end of the cannula and forming with the cannula a working channel sized and configured to receive the instrument;

an elastomeric septum valve disposed in the housing and extending transverse to the axis of the cannula across the working channel;

portions of the septum valve defining a hole having a diameter less than the diameter of the outer surface of the instrument so that during insertion of the instrument along the working channel the septum valve forms a seal with the outer surface of the instrument;

portions of the septum valve being configured to exert a first force on the instrument when the instrument is being inserted into the working channel of the trocar, and to exert a second force on the instrument when the instrument is being withdrawn from the working channel of the trocar, the first force being less than the second force;

portions of the valve defining a proximal surface having the configuration of a funnel extending distally to the hole, the funnel having the shape of a frustrum of a cone;

the valve having a molded state and an operative state with the proximal surface of the valve in the molded state having a generally planar configuration and in the operative state having the funnel configuration; wherein the housing exerts a radial compressive force on the valve in the operative state in order to provide the proximal surface of the valve with the funnel configuration.

19. The trocar recited in claim 18 wherein the housing defines an annular recess having a first diameter and the trocar further comprises:

circumferential portions of the valve having a second diameter greater than the first diameter of the recess; whereby the housing exerts a compressive force on the valve when the valve is operatively disposed in the recess of the housing.

* * * * *